(12) United States Patent
Inoue et al.

(10) Patent No.: US 8,131,037 B2
(45) Date of Patent: Mar. 6, 2012

(54) RADIATION IMAGING APPARATUS AND METHOD OF CONTROLLING THE SAME

(75) Inventors: Chizuru Inoue, Tokyo (JP); Takashi Yoshida, Yokosuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 876 days.

(21) Appl. No.: 12/180,843

(22) Filed: Jul. 28, 2008

(65) Prior Publication Data

US 2009/0046911 A1 Feb. 19, 2009

(30) Foreign Application Priority Data

Aug. 14, 2007 (JP) ................................ 2007-211501

(51) Int. Cl.
*G06K 9/00* (2006.01)
(52) U.S. Cl. ..................................................... 382/128
(58) Field of Classification Search .................... 382/128
See application file for complete search history.

(56) References Cited

U.S. PATENT DOCUMENTS 5,544,215 A * 8/1996 Shroy et al. ................ 378/98.12
(Continued)

FOREIGN PATENT DOCUMENTS

JP 5-192317 8/1993
(Continued)

*Primary Examiner* — Rodney Fuller
(74) *Attorney, Agent, or Firm* — Fitzpatrick, Cella, Harper & Scinto (57) ABSTRACT

A radiation imaging apparatus detects the density distribution of an image formed by a radiopaque dye from each of two images obtained by radiation imaging. The apparatus predicts the moving speed of the image formed by the radiopaque dye based on the moving amount of the detected density distribution and the interval between the radiographing times of the two images, and determines the next timing of radiation imaging based on the predicted moving speed and the detected density distribution. A radiation imaging apparatus detects the density distribution of a radiopaque dye in an image obtained by X-ray radiation imaging and predicts the moving speed of the radiopaque dye based on the change amount of the density distribution. The radiation imaging apparatus determines the X-ray irradiation timing based on the predicted radiopaque dye moving speed, the detected radiopaque dye density distribution, and a predetermined radiopaque dye density.

10 Claims, 8 Drawing Sheets

U.S. PATENT DOCUMENTS

| | | | |
|---|---|---|---|
| 5,682,413 A * | 10/1997 | Wong et al. | 378/98.11 |
| 7,113,817 B1 * | 9/2006 | Winchester et al. | 600/476 |
| 7,689,014 B2 * | 3/2010 | Abovitz et al. | 382/128 |
| 2008/0159481 A1 | 7/2008 | Yoshida | 378/95 |
| 2008/0317205 A1 | 12/2008 | Inuga et al. | 378/97 |

FOREIGN PATENT DOCUMENTS

| | | |
|---|---|---|
| JP | 5-192319 | 8/1993 |

* cited by examiner

- RADIOPAQUE DYE DENSITY fi(P) OF POINT P AT TIME Ti
- PREDICTED RADIOPAQUE DYE DENSITY gi(P) OF POINT P AT TIME Tj WHICH IS PREDICTED AT TIME Ti
- CURRENT TIME (= RADIOGRAPHING TIME OF LATEST IMAGE) T1

RADIATION IMAGING APPARATUS AND METHOD OF CONTROLLING THE SAME

BACKGROUND OF THE INVENTION

1. Field of the Invention

The present invention relates to a radiation imaging apparatus for performing radiation imaging using a radiopaque dye, and a method of controlling the same.

2. Description of the Related Art

Angiography by an X-ray diagnostic imaging apparatus is done using a radiopaque dye. When blood vessels in which a radiopaque dye is injected are radiographed by X-ray radiation imaging, an X-ray absorption difference is generated between the blood vessels and other tissues, and the blood vessel form or blood flow state can be visualized more clearly. This allows the doctor to make a more correct diagnosis or treatment.

A common method of angiography using a radiopaque dye is DSA (Digital Subtraction Angiography). In DSA, an object is radiographed by X-ray radiation imaging to obtain an image before radiopaque dye injection. This image is called a mask image. Next, a radiopaque dye is injected into blood vessels. The object is radiographed by X-ray imaging to obtain an image after radiopaque dye injection. This image is called a contrast image. The difference between the mask image and the contrast image is calculated, and the background including bones and organs is erased, thereby obtaining an angiographic image containing only a blood vessel image.

To generate an angiographic image containing only blood vessels, continuous images are obtained by radiographing the movement of a radiopaque dye over a plurality of frames, and the peak value is obtained at each pixel position. Based on the peak value of each pixel, images with the highest radiopaque dye density are composited to generate a blood vessel angiographic image.

The irradiation for X-ray imaging is performed at a preset fixed frame rate. Generally, a technician sets the frame rate in accordance with the body part to be radiographed. There also exists an apparatus which allows a technician to manually change the frame rate during X-ray imaging.

A technique of determining the frame rate of X-ray imaging is disclosed in Japanese Patent Laid-Open No. 5-192319 (to be referred to as patent reference 1 hereinafter). Patent reference 1 proposes an X-ray diagnostic apparatus which controls X-ray irradiation in accordance with a change in an object. This apparatus raises the frame rate upon determining that a radiopaque dye enters the irradiation field.

However, the prior art has the following problems.

The amount of use of the radiopaque dye is preferably small in order to suppress the side effect. However, when the amount of use is small, it is necessary to perform imaging at a high frame rate without failing to radiograph images. This leads to excess imaging and an increase in the irradiation dose at a portion with a slow blood flow. If imaging is done at a low frame rate to prevent excess irradiation, an imaging failure occurs at a portion with a fast blood flow, and the obtained angiographic image contains breaks in the blood vessels. That is, excess or deficient irradiation occurs depending on the moving speed of the radiopaque dye.

To manually deal with a change in the blood flow velocity, the technician raises the frame rate when the blood flow velocity increases and lowers the frame rate when the blood flow velocity decreases by operating a user interface (UI) while visually observing, on a monitor, the blood vessel image that is being radiographed. In this method, the reaction speed of human eye (human sensation) affects the frame rate adjustment. It is therefore difficult to avoid excess imaging or imaging failure.

In patent reference 1, it is possible to suppress the total irradiation dose of a patient by limiting the high frame rate period to, for example, a period when the radiopaque dye is present in the irradiation field. When determining that the radiopaque dye enters the irradiation field, imaging using a high frame rate is performed. This prevents an imaging failure but cannot solve the problem of the high irradiation dose caused by excess imaging at a portion with a slow blood flow.

SUMMARY OF THE INVENTION

According to a typical aspect of the present invention, there are provided a radiation imaging apparatus capable of acquiring a radiographic image by appropriate irradiation while suppressing the irradiation dose and the radiopaque dye injection amount by controlling the irradiation timing of radiation in accordance with a change in the radiopaque dye moving speed, and a method of controlling the same.

According to one aspect of the present invention, there is provided a radiation imaging apparatus comprising:

a detection unit adapted to detect a density distribution of an image formed by a radiopaque dye from an image obtained by radiation imaging;

a prediction unit adapted to calculate a moving speed of the image formed by the radiopaque dye on the basis of a moving amount of the density distribution detected by the detection unit in two images obtained by radiation imaging and an interval between radiographing times of the two images; and a determination unit adapted to determine a next timing of radiation imaging on the basis of the moving speed calculated by the prediction unit and the density distribution detected by the detection unit.

Also, according to another aspect of the present invention, there is provided a method of controlling a radiation imaging apparatus, comprising:

a detection step of detecting a density distribution of an image formed by a radiopaque dye from an image obtained by radiation imaging;

a prediction step of calculating a moving speed of the image formed by the radiopaque dye on the basis of a moving amount of the density distribution detected in the detection step in two images obtained by radiation imaging and an interval between radiographing times of the two images; and a determination step of determining a next timing of radiation imaging on the basis of the moving speed calculated in the prediction step and the density distribution detected in the detection step.

Further features of the present invention will become apparent from the following description of exemplary embodiments with reference to the attached drawings.

DESCRIPTION OF THE EMBODIMENTS

Exemplary embodiments of the present invention will now be described in detail in accordance with the accompanying drawings.

First Embodiment

Figure 1:
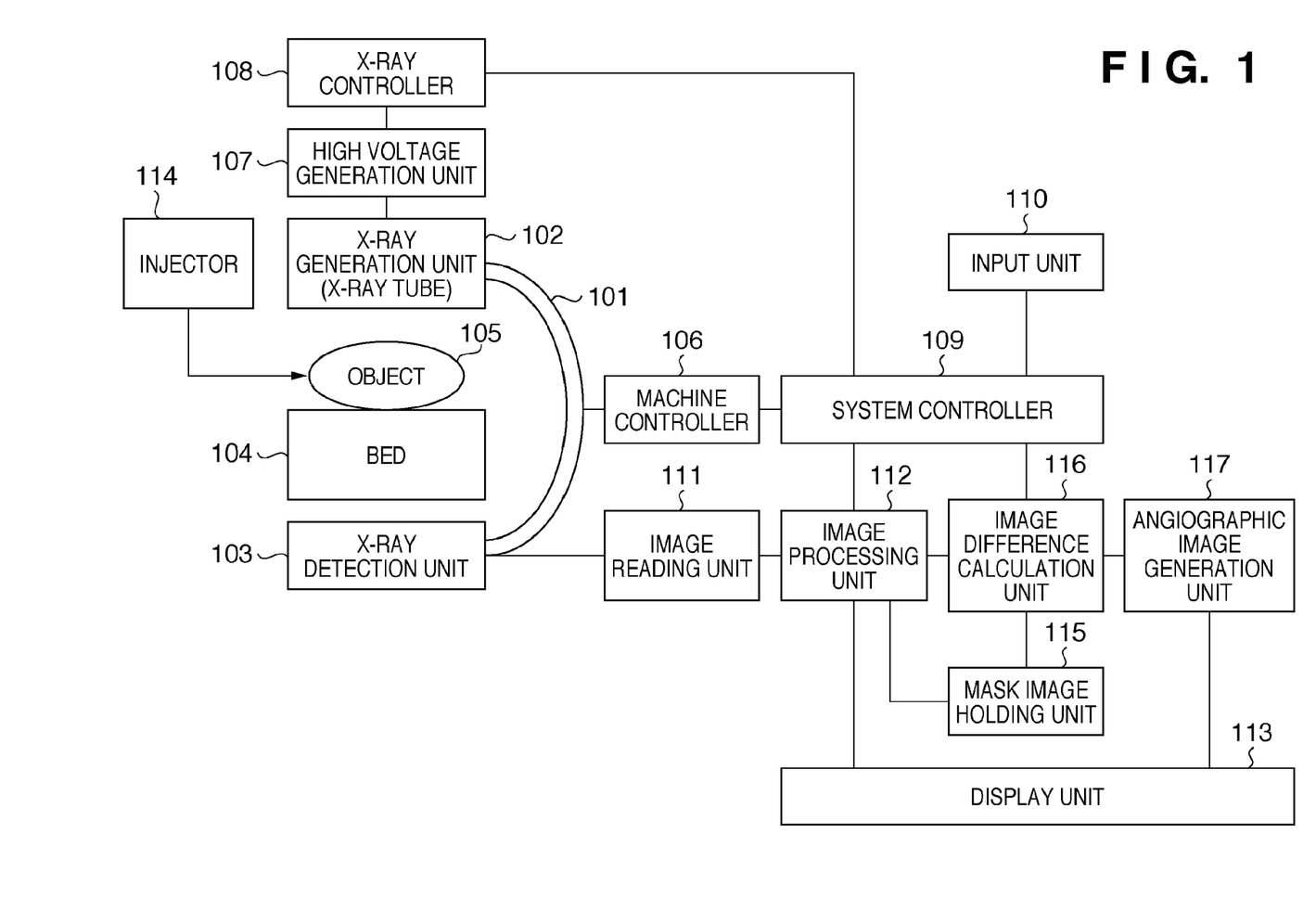
FIG. 1 is a block diagram showing an example of the arrangement of an X-ray diagnostic imaging apparatus according to an embodiment.

FIG. 1 is a block diagram showing an example of the arrangement of an X-ray diagnostic imaging apparatus according to this embodiment. In this embodiment, an X-ray diagnostic imaging apparatus for performing X-ray imaging will be exemplified as a radiation imaging apparatus for performing radiation imaging. In the X-ray diagnostic imaging apparatus, a holding unit 101 has an X-ray generation unit (X-ray tube) 102 stationarily supported at an end as an X-ray generation source, and an X-ray detection unit 103 stationarily supported at the other end as an X-ray detection means. With this structure, the holding unit 101 stationarily supports the X-ray generation unit 102 and the X-ray detection unit 103, which oppose each other. A bed 104 is provided between the X-ray generation unit 102 and the X-ray detection unit 103. The bed 104 has a top plate (not shown) and leg portions (not shown) that support the top plate. An object 105, that is, a patient is placed on the top plate. The top plate is movable in necessary directions, for example, vertically and horizontally.

Each of the top plate (not shown) of the bed 104 and the holding unit 101 has a motor (not shown) and a position sensor (not shown). The motors and position sensors are connected to a machine controller 106. The machine controller 106 controls the motors in accordance with sensor information from the position sensors and drives the top plate of the bed 104 and the holding unit 101 so that they have a required positional relationship.

The X-ray generation unit 102 is connected to a high voltage generation unit 107. The X-ray generation unit 102 receives a necessary voltage from the high voltage generation unit 107 and irradiates the object 105 with X-rays. The high voltage generation unit 107 is connected to an X-ray controller 108. The X-ray controller 108 controls the high voltage generation unit 107, thereby controlling the dose of X-rays to be output from the X-ray generation unit 102 during imaging or fluorography. The machine controller 106 and X-ray controller 108 are connected to a system controller 109 and controlled by it.

The X-ray detection unit 103 is connected to an image reading unit 111 which reads out image data from the X-ray detection unit 103. The image reading unit 111 is connected to an image processing unit 112. The image processing unit 112 processes the image data read by the image reading unit 111.

A display unit 113 is connected to the image processing unit 112 and an angiographic image generation unit 117 and displays image data processed by the image processing unit 112 or an image based on angiographic image data generated by the angiographic image generation unit 117. The display unit 113 also displays object information (e.g., name, age, sex, length, weight, and imaging or fluoroscopy target body part) and imaging and fluoroscopic conditions including X-ray conditions.

Various kinds of controllers such as the machine controller 106 and X-ray controller 108, an input unit 110, the image processing unit 112, and an image difference calculation unit 116 are connected to the system controller 109. The input unit 110 includes a keyboard, mouse, touch panel, membrane buttons, and joystick, and an irradiation switch or foot pedal to give a trigger to start or stop irradiation. The image processing unit 112 executes image processing such as gamma correction or noise reduction. The image difference calculation unit 116 generates an angiographic image. Note that the imaging and fluoroscopic conditions and the object information (e.g., name, age, sex, length, weight, and imaging or fluoroscopy target body part) are input from the input unit 110.

An injector 114 is a tool for injecting a radiopaque dye in a blood vessel of the object 105. The radiopaque dye is injected in a predetermined part of the object 105 in accordance with the diagnostic part. A mask image holding unit 115, image difference calculation unit 116, and angiographic image generation unit 117 are components to be used for angiography using a radiopaque dye. The mask image holding unit 115 holds, in a storage unit (e.g., RAM 202), image data (mask image) before radiopaque dye injection which is processed by the image processing unit 112. The image difference calculation unit 116 executes a subtraction process of calculating the difference between the mask image obtained from the mask image holding unit 115 and an image (contrast image) after radiopaque dye injection obtained from the image processing unit 112. The angiographic image generation unit 117 generates an angiographic image based on the image data obtained by the image difference calculation unit 116.

Figure 2:
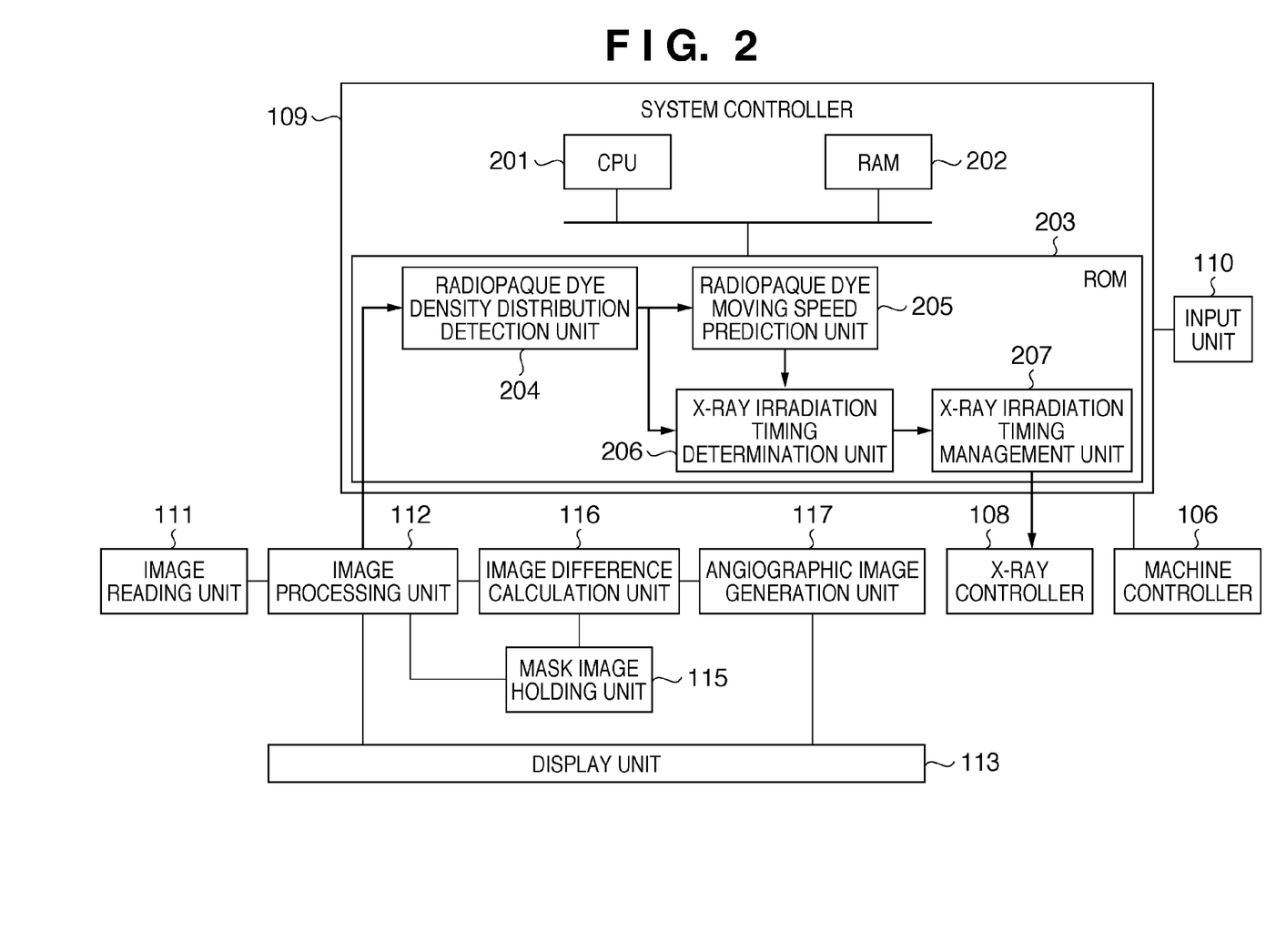
FIG. 2 is a block diagram showing an example of the functional arrangement of the system controller of the X-ray diagnostic imaging apparatus according to the embodiment.

FIG. 2 is a block diagram showing an example of the functional arrangement of the system controller 109 of the X-ray diagnostic imaging apparatus shown in FIG. 1.

The system controller 109 includes a CPU 201 which implements the procedure of flowcharts to be described later, the RAM 202 functioning as the main memory or work memory of the CPU 201, and a ROM 203 storing programs. The ROM 203 stores programs which cause the CPU 201 to function as a radiopaque dye density distribution detection unit 204, radiopaque dye moving speed prediction unit 205, X-ray irradiation timing determination unit 206, and X-ray irradiation timing management unit 207.

The radiopaque dye density distribution detection unit 204 analyzes image data obtained from the image processing unit 112, thereby detecting the radiopaque dye density distribution in the image. The radiopaque dye moving speed prediction unit 205 calculates the moving speed of an image formed by the radiopaque dye based on the amount of change (moving amount) of the radiopaque dye density distribution between two images obtained from the radiopaque dye density distribution detection unit 204. This speed is called the predicted moving speed of the radiopaque dye. More specifically, the radiopaque dye moving speed prediction unit 205 calculates the moving speed of the image formed by the radiopaque dye based on the amount of movement of the density distribution between two images obtained upon X-ray imaging and the interval between the radiographing times of the images.

The X-ray irradiation timing determination unit 206 determines the X-ray irradiation timing based on a predetermined radiopaque dye density, the radiopaque dye density distribution detected by the radiopaque dye density distribution detection unit 204, and the predicted moving speed of the radiopaque dye calculated by the radiopaque dye moving speed prediction unit 205. Note that the predetermined radiopaque dye density is a radiopaque dye density value necessary for generating an angiographic image in consideration of noise and the like. The process of the X-ray irradiation timing determination unit 206 will be described later in detail with reference to the flowchart in FIG. 4.

The X-ray irradiation timing management unit 207 has a function of holding the X-ray irradiation timing in a storage unit (e.g., RAM 202) and manages the X-ray irradiation timing. In accordance with the value held by the X-ray irradiation timing management unit 207, the X-ray controller 108 is controlled to perform X-ray irradiation.

Figure 3:
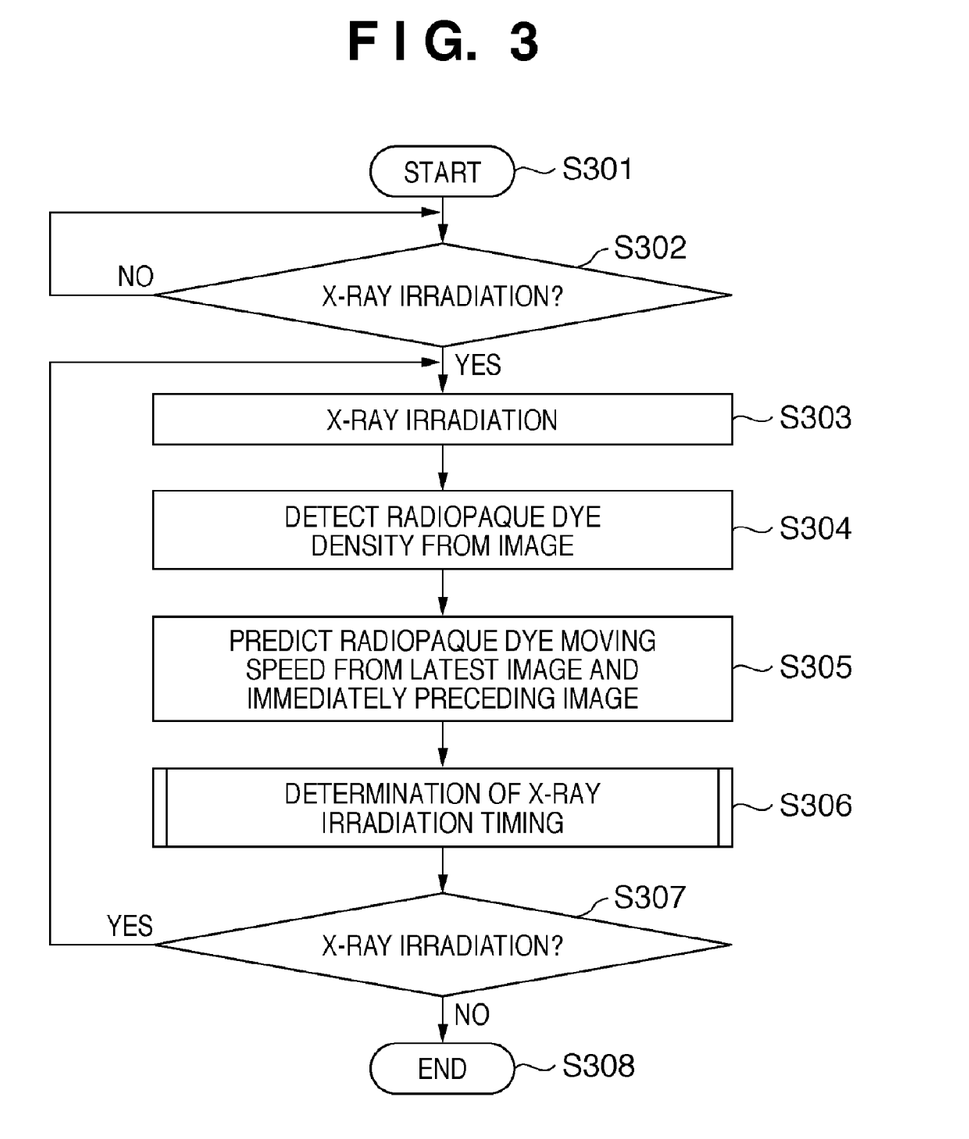
FIG. 3 is a flowchart illustrating an X-ray irradiation process according to the first embodiment.

FIG. 3 is a flowchart illustrating the operation of the X-ray diagnostic imaging apparatus according to the first embodiment.

Step S301 is the start point of the process. In step S302, the CPU 201 determines whether a trigger to start X-ray irradiation is given. The trigger to start X-ray irradiation is given by, for example, pressing the foot pedal or irradiation switch of the input unit 110. If it is determined that the trigger to start X-ray irradiation is given, the process advances to step S303. Otherwise, the process returns to step S302. That is, in step S302, the process waits until the trigger to start irradiation is detected by polling or the like. Upon detecting the trigger to start irradiation, the process advances to step S303.

In step S303, the X-ray irradiation timing management unit 207 sends an instruction to the X-ray controller 108 to perform X-ray irradiation based on the X-ray irradiation timing held in the storage unit (the RAM 202 in this embodiment). Note that as the initial value of the X-ray irradiation timing, a preset default value or a value set by a technician before the operation is held.

In step S304, the radiopaque dye density distribution detection unit 204 detects the radiopaque dye density distribution for the radiographed image. The density distribution is detected by image processing. More specifically, the density distribution is detected by calculating the amount of change of the luminance value of each pixel that was, for example, formerly bright and abruptly darkened. That is, the radiopaque dye density distribution is obtained by specifying the existence range of the radiopaque dye in the image based on the change in the luminance value of each pixel and detecting the density distribution in the existence range of the radiopaque dye.

In step S305, the radiopaque dye moving speed prediction unit 205 acquires the point with the highest radiopaque dye density from each of the radiopaque dye density distribution in the latest radiographed image detected in step S304 and the radiopaque dye density distribution in the immediately preceding radiographed image. Based on the moving distance of the point with the highest density and the interval between the density distribution detection times (the interval between the radiographing times of the two images), the radiopaque dye moving speed prediction unit 205 calculates the moving speed of the radiopaque dye as the next predicted moving speed of the radiopaque dye. Note that the moving distance is the distance along the image of the radiopaque dye. For example, if P1min moves to P1max in a blood vessel image shown in FIG. 5, the distance along the curve of the blood vessel image is calculated as the moving distance.

In step S306, the X-ray irradiation timing determination unit 206 determines the X-ray irradiation timing. The X-ray irradiation timing is determined based on the information of the radiopaque dye density distribution detected in step S304, the predicted moving speed of the radiopaque dye calculated in step S305, and a predetermined radiopaque dye density necessary for generating an angiographic image. That is, the X-ray irradiation timing is updated as needed as the moving speed of the radiopaque dye varies. This process will be described later in detail with reference to the flowchart in FIG. 4.

In step S307, the CPU 201 determines whether a trigger for X-ray irradiation is given. The trigger for X-ray irradiation is given by pressing the foot pedal or irradiation switch, as in step S302. If it is determined that the trigger for irradiation is given, the process returns to step S303. Otherwise, the process advances to step S308. Step S308 is the end point of the algorithm.

Figure 4:
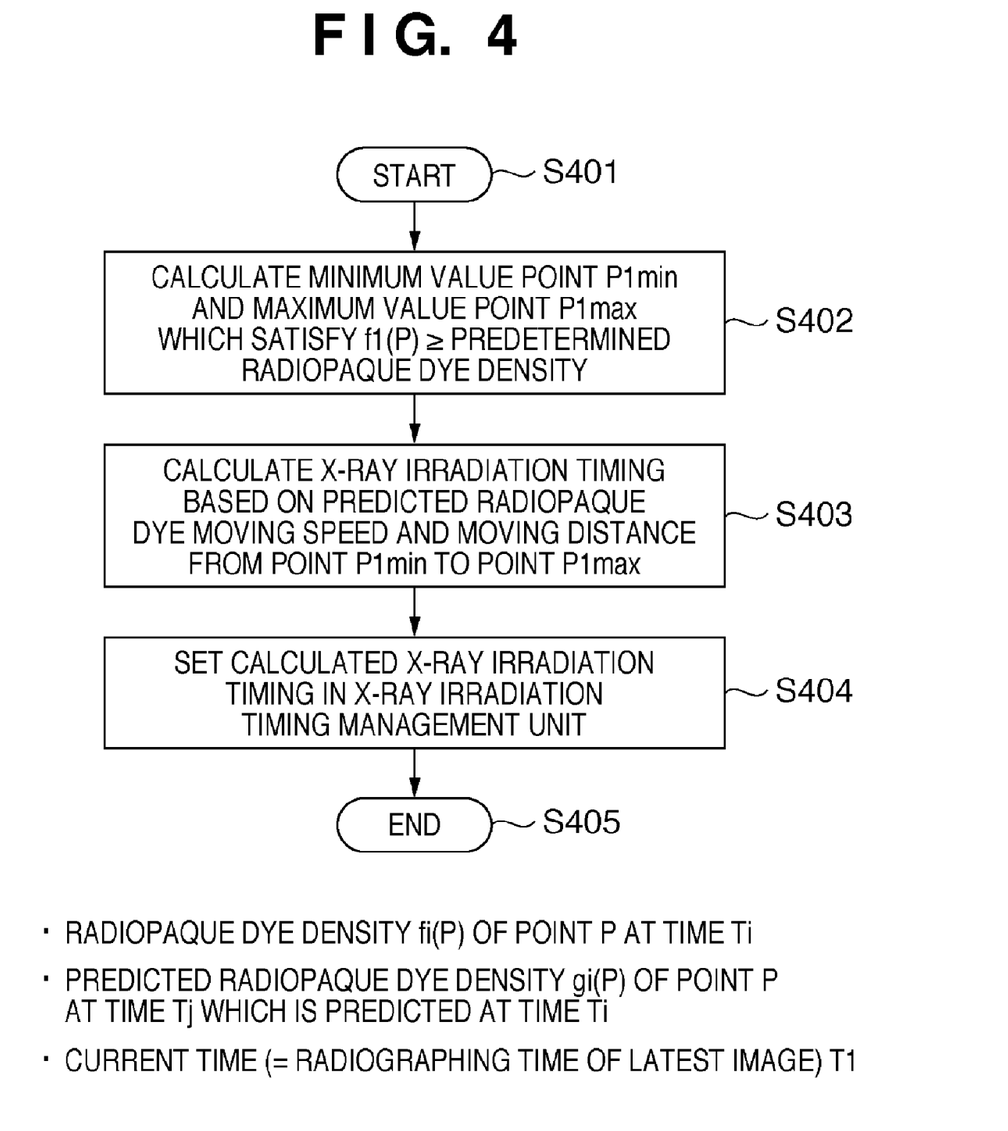
FIG. 4 is a flowchart illustrating a process of determining the X-ray irradiation timing by the system controller according to the first embodiment.

FIG. 4 is a flowchart illustrating a process of causing the X-ray irradiation timing determination unit 206 to determine the X-ray irradiation timing (the process in step S306 of FIG. 3). The process sequence will be explained also using the graph in FIG. 6 which shows the relationship between the moving distance and density of a radiopaque dye and the X-ray irradiation timing.

Let fi (P) be the radiopaque dye density of a point P at time Ti, and gi (P) be the predicted radiopaque dye density of the point P at future time Tj. The density gi (P) is predicted based on fi (P) assuming that the radiopaque dye density distribution does not relatively change in a short time. The radiographing time of the latest image is defined as T1.

Figure 6:
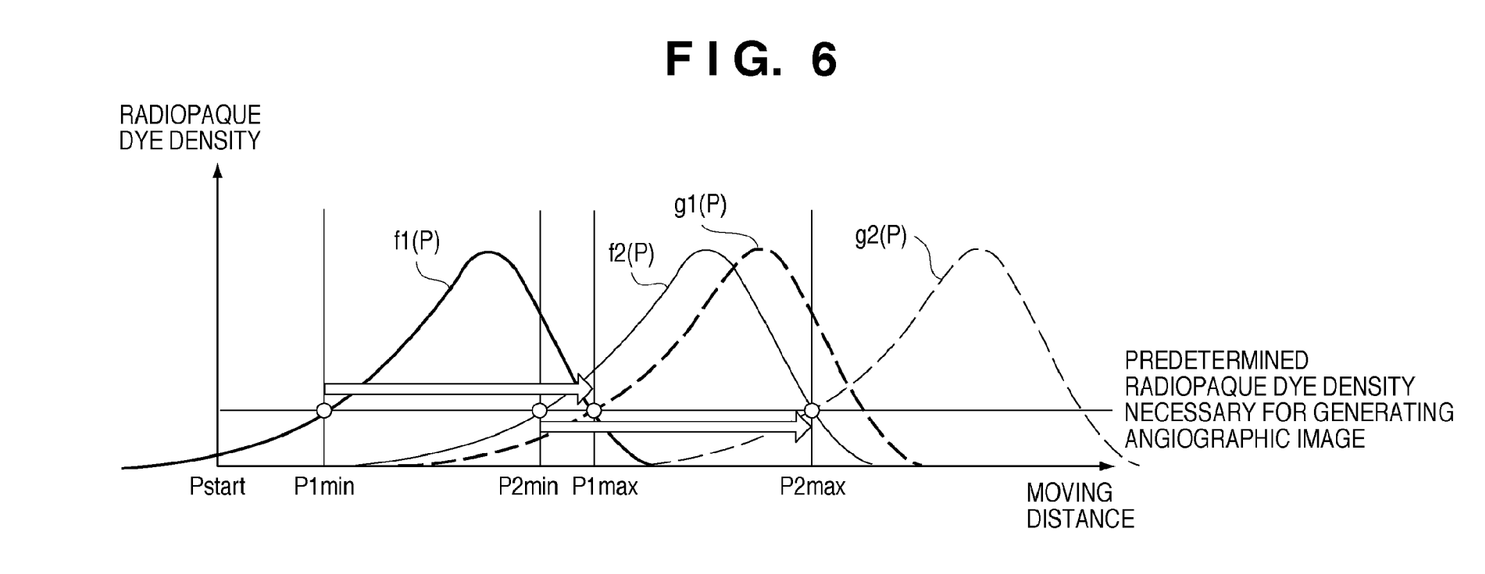
FIG. 6 is a graph showing the relationship between the moving distance and density of a radiopaque dye and the X-ray irradiation timing according to the first embodiment.

Step S401 is the start point of the algorithm. In step S402, the X-ray irradiation timing determination unit 206 calculates an end point P1min and a leading point P1max of a blood vessel image where a radiopaque dye density f1(P) of the point P at the time T1 exceeds the predetermined radiopaque dye density necessary for generating an angiographic image. The end point and leading point are the end point and start point of the radiopaque dye in a blood vessel which satisfy the following condition. That is, the minimum value P1min and maximum value P1max of the point P shown in FIG. 6, which satisfy $$f1(P) \geq \text{predetermined radiopaque dye density}$$

are calculated.

In step S403, the X-ray irradiation timing determination unit 206 determines the X-ray irradiation timing based on the predicted moving speed of the radiopaque dye calculated in step S305 of FIG. 3, and the moving distance from the point P1min to the point P1max calculated in step S402. The X-ray irradiation timing is the timing at which P1min reaches P1max when the radiopaque dye moves at the predicted moving speed. Hence, the next X-ray irradiation timing T2 is given by $$T2 = T1 + (P1\text{max} - P1\text{min})/\text{predicted moving speed}$$

That is, the timing at which f1(P) in FIG. 6 matches g1(P) is determined as the X-ray irradiation timing.

In step S404, the X-ray irradiation timing determination unit 206 sets the X-ray irradiation timing calculated in step S403 in the X-ray irradiation timing management unit 207. Step S405 is the end point of the algorithm.

Figure 5:
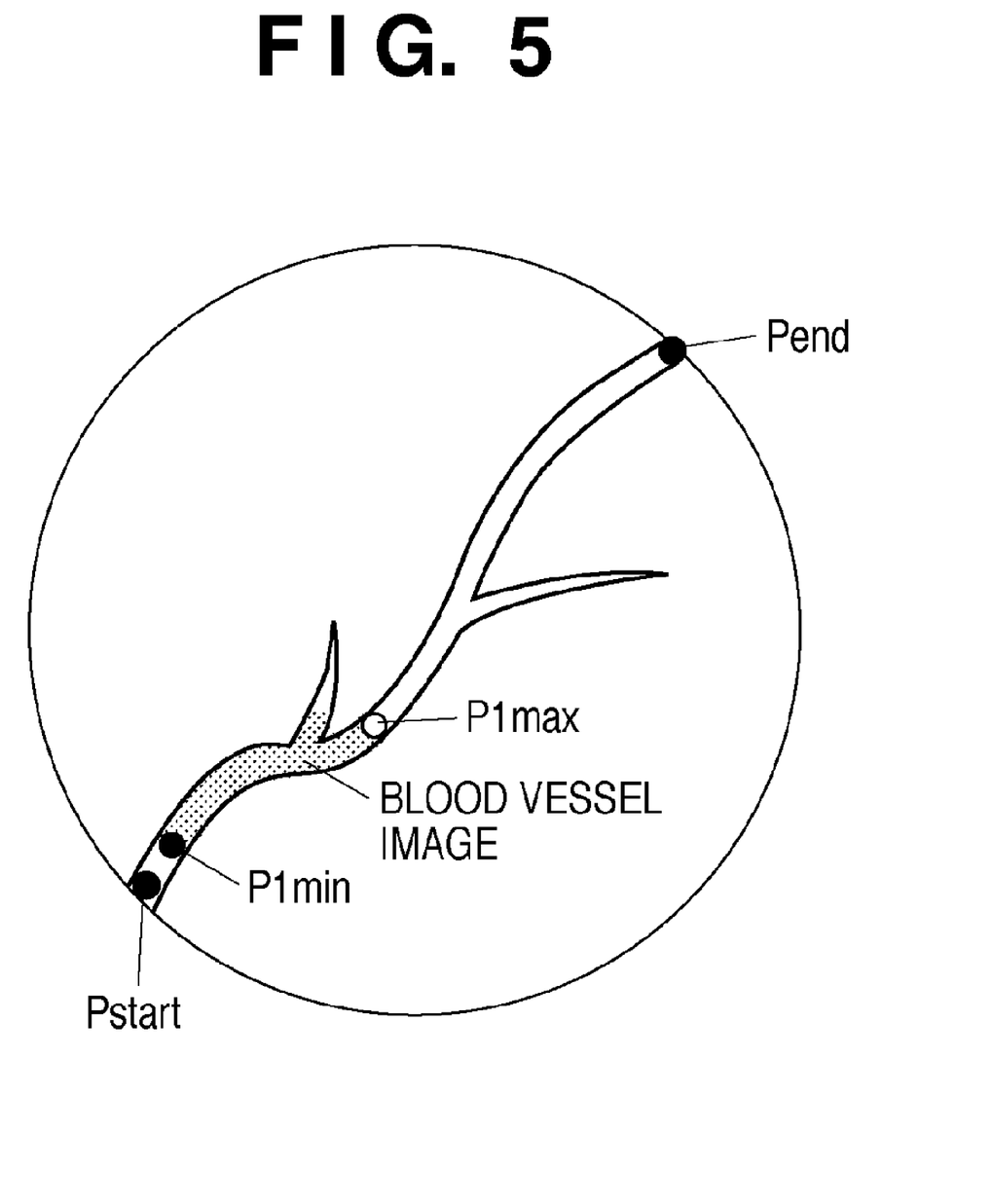
FIG. 5 is a view showing an example of a blood vessel image radiographed by the X-ray diagnostic imaging apparatus.

FIG. 5 is a view showing a blood vessel image radiographed by the X-ray diagnostic imaging apparatus. The blood is assumed to flow from a point Pstart to a point Pend.

FIG. 6 will be described next in detail. FIG. 6 is a graph showing the relationship between the moving distance and density of the radiopaque dye and the X-ray irradiation timing according to the first embodiment. Referring to FIG. 6, the ordinate represents the density of the radiopaque dye, and the abscissa represents the moving distance of the blood flow from the point Pstart to the point Pend in FIG. 5. Additionally, f1(P) is the actual radiopaque dye density distribution of the point P at the time T1, g1(P) is the predicted radiopaque dye density distribution of the point P at the time T2, which is predicted at the time T1, f2(P) is the actual radiopaque dye density distribution of the point P at the time T2, g2(P) is the predicted radiopaque dye density distribution of the point P at time T3, which is predicted at the time T2, P1min is the minimum value (end point) that satisfies "f1(P)≧predetermined radiopaque dye density", P1max is the maximum value (leading point) that satisfies "f1(P)≧predetermined radiopaque dye density", P2min is the minimum value (end point) that satisfies "f2(P)≧predetermined radiopaque dye density", and P2max is the maximum value (leading point) that satisfies "f2(P)≧predetermined radiopaque dye density".

However, g1(P) and g2(P) are predicted based on f1(P) and f2(P), respectively, assuming that the radiopaque dye density distribution does not relatively change in a short time. The X-ray irradiation timing determination unit 206 of the first embodiment determines the next X-ray irradiation timing based on the moving speed calculated by the radiopaque dye moving speed prediction unit 205 and the radiopaque dye density distribution detected by the radiopaque dye density distribution detection unit 204. For example, the X-ray irradiation timing determination unit 206 determines the next timing of radiation imaging so that an image having a predetermined radiopaque dye density or more in the image obtained by the latest radiation imaging is jointed with that in the image to be obtained by the next radiation imaging. That is, the next timing of radiation imaging is determined such that the image of f1(P) and the image of g1(P) are jointed at the position of the predetermined radiopaque dye density. In this embodiment, the next timing of radiation imaging is determined such that the images are jointed at the position of the minimum and necessary radiopaque dye density for generating an angiographic image as the predetermined radiopaque dye density, that is, such that P1min changes to P1max. At and near the timing when the radiopaque dye enters the screen, Pmin matches Pstart. Similarly, at the timing when the radiopaque dye leaves the screen, Pmax matches Pend.

In the first embodiment, the radiopaque dye density distribution detection method of the radiopaque dye density distribution detection unit 204 is not limited to that in step S304 of FIG. 3. The predicted radiopaque dye moving speed calculation method of the radiopaque dye moving speed prediction unit 205 is not limited to that in step S305 of FIG. 3 (calculating the moving distance based on the point with the highest radiopaque dye density between two images and calculating the predicted moving speed). For example, a method of calculating the moving distance of "the leading point of the radiopaque dye image having the predetermined radiopaque dye density or more" between two images and calculating the predicted moving speed may be employed.

Second Embodiment

X-ray irradiation control of a system controller 109 according to the second embodiment is the same as in the first embodiment (the process illustrated by the flowchart in FIG. 3). The different point is a process of causing an X-ray irradiation timing determination unit 206 to determine the X-ray irradiation timing (the process in step S306 of FIG. 3).

Figure 7:
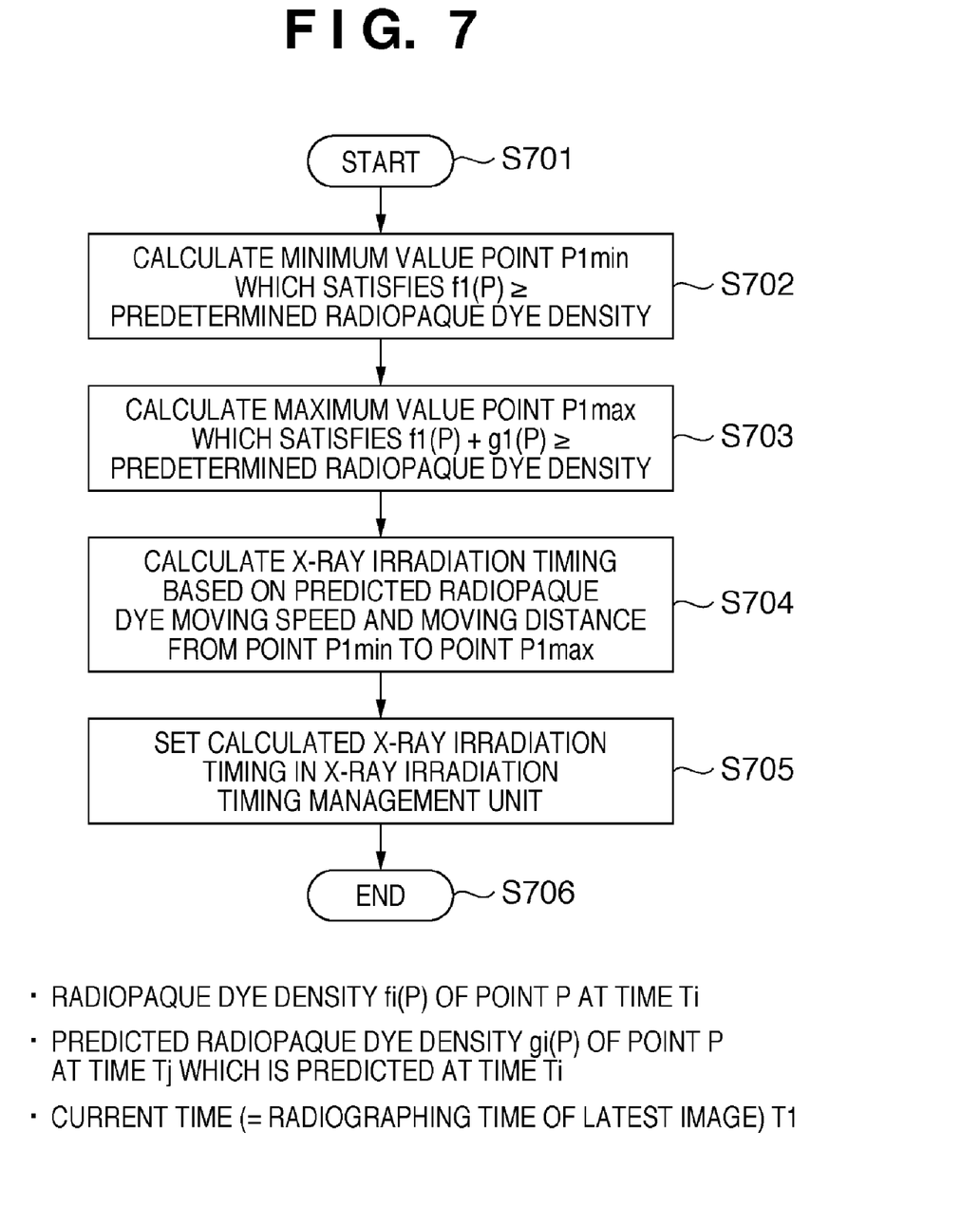
FIG. 7 is a flowchart illustrating a process of determining the X-ray irradiation timing by a system controller according to the second embodiment.
Figure 8:
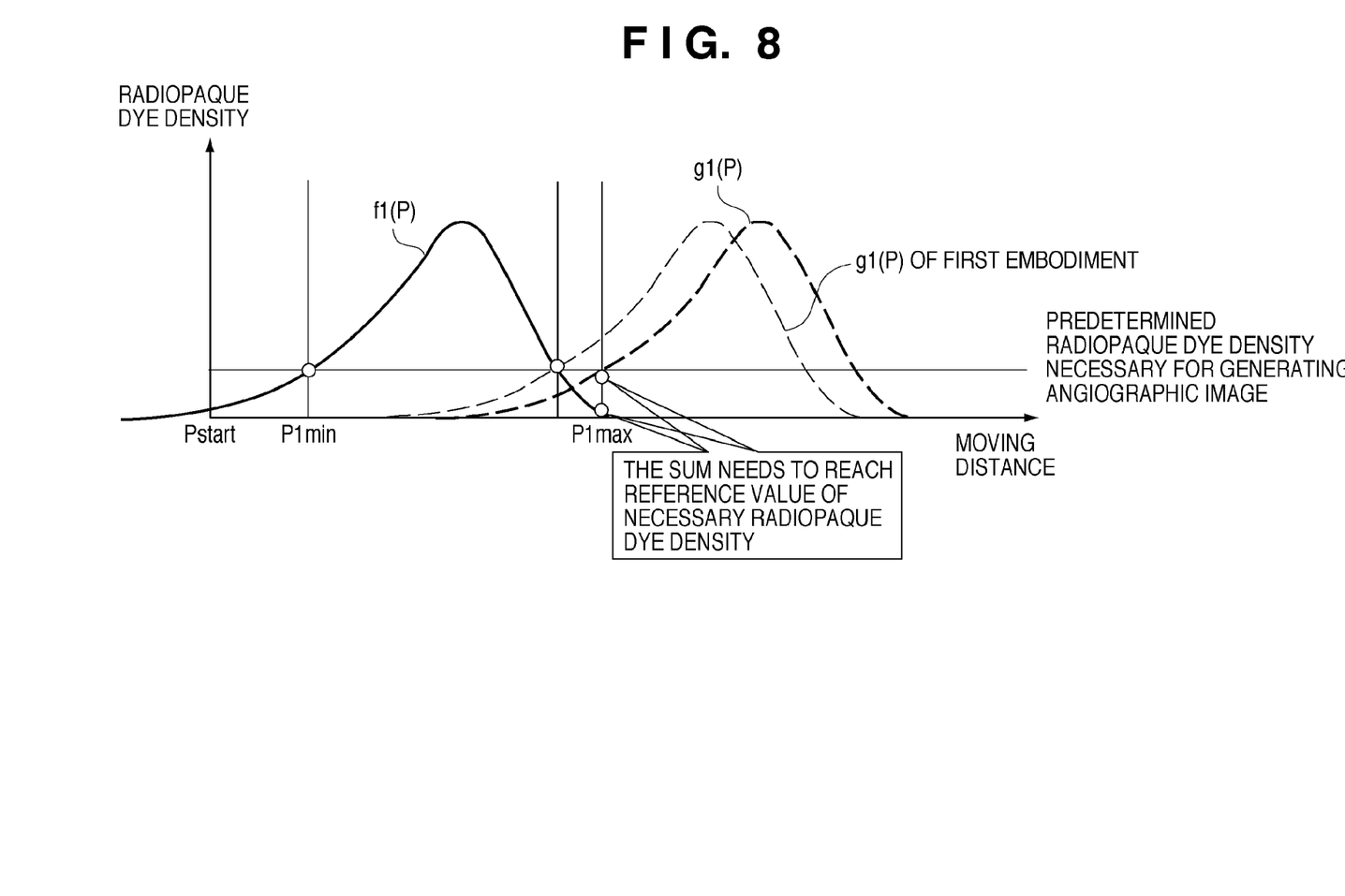
FIG. 8 is a graph showing the relationship between the moving distance and density of a radiopaque dye and the X-ray irradiation timing according to the second embodiment.

FIG. 7 is a flowchart illustrating the process of causing the X-ray irradiation timing determination unit 206 to determine the X-ray irradiation timing (the process in step S306 of FIG. 3) according to the second embodiment. The process sequence will be explained also using the graph in FIG. 8 which shows the relationship between the moving distance and density of a radiopaque dye and the X-ray irradiation timing. FIG. 8 will be described later in detail.

Let fi (P) be the radiopaque dye density of a point P at time Ti, and gi (P) be the predicted radiopaque dye density of the point P at future time Tj. The density gi (P) is predicted based on fi (P) assuming that the radiopaque dye density distribution does not relatively change in a short time. The radiographing time of the latest image is defined as T1.

Step S701 is the start point of the algorithm. In step S702, the X-ray irradiation timing determination unit 206 calculates an end point P1min of a blood vessel image where a radiopaque dye density f1(P) of the point P at the time T1 exceeds the predetermined radiopaque dye density necessary for generating an angiographic image. The end point is the end point of the radiopaque dye in a blood vessel which satisfy the above-described condition. That is, the minimum value P1min shown in FIG. 8, which satisfies $f1(P) \geqq$ predetermined radiopaque dye density is calculated.

In step S703, the X-ray irradiation timing determination unit 206 calculates P1max. P1max is the leading point of the blood vessel image where the sum of the radiopaque dye density f1(P) of the point P at the time T1 and a predicted radiopaque dye density g1(P) of the point P at time T2, which is predicted at the time T1, exceeds the predetermined radiopaque dye density. The leading point is the start point of the radiopaque dye in the blood vessel which satisfies the above-described condition. That is, the maximum value P1max shown in FIG. 8, which satisfies $f1(P)+g1(P) \geqq$ predetermined radiopaque dye density
(for $f1(P)>0$)

is calculated.

In step S704, the X-ray irradiation timing determination unit 206 determines the X-ray irradiation timing. The X-ray irradiation timing is determined using the predicted moving speed of the radiopaque dye calculated in step S305 of FIG. 3, and the moving distance from the point P1min calculated in step S702 to the point P1max calculated in step S703. The X-ray irradiation timing is the timing at which P1min reaches P1max when the radiopaque dye moves at the predicted moving speed. Hence, the next X-ray irradiation timing T2 is given by $T2=T1+(P1max-P1min)/$predicted moving speed That is, the timing at which f1(P) in FIG. 8 matches g1(P) is determined as the X-ray irradiation timing.

In step S705, the X-ray irradiation timing determination unit 206 sets the X-ray irradiation timing calculated in step S704 in an X-ray irradiation timing management unit 207. Step S706 is the end point of the algorithm.

FIG. 8 is a graph showing the relationship between the moving distance and density of the radiopaque dye and the X-ray irradiation timing according to the second embodiment. Referring to FIG. 8, the ordinate represents the density of the radiopaque dye, and the abscissa represents the moving distance of the blood flow from a point Pstart to a point Pend in FIG. 5. Additionally, f1(P) is the actual radiopaque dye density distribution of the point P at the time T1, g1(P) is the predicted radiopaque dye density distribution of the point P at the time T2, which is predicted at the time T1, P1min is the minimum value (end point) that satisfies "f1(P)≧predetermined radiopaque dye density", and P1max is the maximum value (leading point) that satisfies "f1(P)+g1(P)≧predetermined radiopaque dye density".

However, the density g1(P) is predicted based on f1(P), assuming that the radiopaque dye density distribution does not relatively change in a short time.

As described above, according to the second embodiment, the next timing of radiation imaging is determined based on the moving speed calculated by a radiopaque dye moving speed prediction unit 205 and the radiopaque dye density distribution detected by a radiopaque dye density distribution detection unit 204. In the second embodiment, the longest timing at which the sum of the radiopaque dye density distributions acquired from the image obtained by the latest radiation imaging and the image to be obtained by the next radiation imaging is always equal to or higher than a predetermined radiopaque dye density is employed.

In the first and second embodiments, the present invention has been described using angiography using a radiopaque dye. However, the present invention is also applicable to contrastradiography except for angiography and, for example, to contrastradiography of an organ using a radiopaque dye such as barium. In an organ, the radiopaque dye moves on its walls, unlike angiography. However, it is possible to calculate the moving distance based on the "point with the highest radiopaque dye density" of two images, as in angiography.

Other Embodiments

The embodiments have been described above in detail. The present invention can also take a form of, for example, a system, apparatus, method, program, or storage medium. More specifically, the present invention is applicable to a system including a plurality of devices or an apparatus including a single device.

The present invention also incorporates a case in which the functions of the above-described embodiments are achieved by supplying a software program to the system or apparatus directly or from a remote site and causing the computer of the system or apparatus to read out and execute the supplied program codes. In this case, the supplied program is a computer program corresponding to the illustrated flowcharts of the embodiments.

Hence, the program codes themselves which are installed in a computer to implement the functional processing of the present invention also implement the present invention. That is, the present invention also incorporates the computer program itself to implement its functional processing.

In this case, the program can take any form such as an object code, a program to be executed by an interpreter, or script data to be supplied to the OS as long as the functions of the program are available.

Examples of a computer-readable storage medium to supply the program are a floppy® disk, hard disk, optical disk, magnetooptical disk, MO, CD-ROM, CD-R, CD-RW, magnetic tape, nonvolatile memory card, ROM, and DVD (DVD-ROM, DVD-R).

The following program supply method is also available. A client computer may connect to a homepage on the Internet via a browser to download the computer program of the present invention from the homepage to a recording medium such as a hard disk. In this case, the downloaded program may a compressed file including an automatic installation function. The program codes contained in the program of the present invention may be divided into a plurality of files so that the user can download the files from different homepages. That is, a WWW server which causes a plurality of users to download the program file to cause a computer to implement the functional processing of the present invention is also incorporated in the present invention.

The program of the present invention may be encrypted, stored in a storage medium such as a CD-ROM, and distributed to users. Any user who satisfies predetermined conditions can download key information for decryption from a homepage via the Internet. The user can execute the encrypted program by using the key information and install the program in the computer.

The functions of the above-described embodiments are implemented when the computer executes the readout program. The functions of the above-described embodiments may also be implemented in cooperation with, for example, the OS running on the computer based on the instructions of the program. In this case, the OS or the like partially or wholly executes actual processing so that the functions of the above-described embodiments are implemented.

The functions of the above-described embodiments may also be partially or wholly implemented by writing the program read out from the recording medium in the memory of a function expansion board inserted into the computer or a function expansion unit connected to the computer. In this case, the program is written in the function expansion board or function expansion unit, and then, the CPU of the function expansion board or function expansion unit partially or wholly executes actual processing based on the instructions of the program.

As described above, according to the present invention, the radiation irradiation timing is controlled in accordance with a change in the moving speed of a radiopaque dye. It is therefore possible to obtain a DSA image by appropriate irradiation while suppressing the irradiation dose and the amount of radiopaque dye injection.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-211501, filed Aug. 14, 2007, which is hereby incorporated by reference herein in its entirety.

What is claimed is:

1. A radiation imaging apparatus comprising:
a detection unit adapted to detect a density distribution of an image formed by a radiopaque dye from an image obtained by radiation imaging;
a prediction unit adapted to calculate a moving speed of the image formed by the radiopaque dye on the basis of a moving amount of the density distribution detected by said detection unit in two images obtained by radiation imaging and an interval between radiographing times of the two images; and
a determination unit adapted to determine a next timing of radiation imaging on the basis of the moving speed calculated by said prediction unit and the density distribution detected by said detection unit,
wherein said determination unit determines the next timing of radiation imaging to joint portions having not less than a predetermined radiopaque dye density in the density distribution when the density distribution detected by said detection unit moves at the moving speed calculated by said prediction unit.

2. The apparatus according to claim 1, wherein said prediction unit calculates, as a moving amount of the density distribution, a moving amount of a position with a highest density in the density distribution detected by said detection unit in the two images.

3. A radiation imaging apparatus comprising:
a detection unit adapted to detect a density distribution of an image formed by a radiopaque dye from an image obtained by radiation imaging;
a prediction unit adapted to calculate a moving speed of the image formed by the radiopaque dye on the basis of a moving amount of the density distribution detected by said detection unit in two images obtained by radiation imaging and an interval between radiographing times of the two images; and
a determination unit adapted to determine a next timing of radiation imaging on the basis of the moving speed calculated by said prediction unit and the density distribution detected by said detection unit,
wherein said determination unit determines the next timing of radiation imaging to, at a connection portion between the density distribution of an image obtained by latest radiation imaging and the density distribution of an image after movement, make a sum of the density distributions equal a predetermined radiopaque dye density when the density distribution detected by said detection unit moves at the moving speed calculated by said prediction unit.

4. The apparatus according to claim 3, wherein said prediction unit calculates, as a moving amount of the density distribution, a moving amount of a position with a highest density in the density distribution detected by said detection unit in the two images.

5. A method of controlling a radiation imaging apparatus, comprising:
a detection step of detecting a density distribution of an image formed by a radiopaque dye from an image obtained by radiation imaging;
a prediction step of calculating a moving speed of the image formed by the radiopaque dye on the basis of a moving amount of the density distribution detected in said detection step in two images obtained by radiation imaging and an interval between radiographing times of the two images; and
a determination step of determining a next timing of radiation imaging on the basis of the moving speed calculated in said prediction step and the density distribution detected in said detection step,
wherein, in said determination step, the next timing of radiation imaging is determined to joint portions having not less than a predetermined radiopaque dye density in the density distribution when the density distribution detected in said detection step moves at the moving speed calculated in said prediction step.

6. The method according to claim 5, wherein, in said prediction step, a moving amount of a position with a highest density in the density distribution detected in said detection step in the two images is calculated as a moving amount of the density distribution.

7. A method of controlling a radiation imaging apparatus, comprising:
a detection step of detecting a density distribution of an image formed by a radiopaque dye from an image obtained by radiation imaging;
a prediction step of calculating a moving speed of the image formed by the radiopaque dye on the basis of a moving amount of the density distribution detected in said detection step in two images obtained by radiation imaging and an interval between radiographing times of the two images; and
a determination step of determining a next timing of radiation imaging on the basis of the moving speed calculated in said prediction step and the density distribution detected in said detection step,
wherein, in said determination step, the next timing of radiation imaging is determined to, at a connection portion between the density distribution of an image obtained by latest radiation imaging and the density distribution of an image after movement, make a sum of the density distributions equal a predetermined radiopaque dye density when the density distribution detected in said detection step moves at the moving speed calculated in said prediction step.

8. The method according to claim 7, wherein, in said prediction step, a moving amount of a position with a highest density in the density distribution detected in said detection step in the two images is calculated as a moving amount of the density distribution.

9. A non-transitory computer-readable storage medium storing a computer program which causes a computer to control a radiation imaging apparatus, the computer program causing the computer to execute:
a detection step of detecting a density distribution of an image formed by a radiopaque dye from an image obtained by radiation imaging;
a prediction step of calculating a moving speed of the image formed by the radiopaque dye on the basis of a moving amount of the density distribution detected in said detection step in two images obtained by radiation imaging and an interval between radiographing times of the two images; and
a determination step of determining a next timing of radiation imaging on the basis of the moving speed calculated in said prediction step and the density distribution detected in said detection step,
wherein, in said determination step, the next timing of radiation imaging is determined to joint portions having not less than a predetermined radiopaque dye density in the density distribution when the density distribution detected in said detection step moves at the moving speed calculated in said prediction step.

10. A non-transitory computer-readable storage medium storing a computer program which causes a computer to control a radiation imaging apparatus, the computer program causing the computer to execute:
a detection step of detecting a density distribution of an image formed by a radiopaque dye from an image obtained by radiation imaging;
a prediction step of calculating a moving speed of the image formed by the radiopaque dye on the basis of a moving amount of the density distribution detected in said detection step in two images obtained by radiation imaging and an interval between radiographing times of the two images; and
a determination step of determining a next timing of radiation imaging on the basis of the moving speed calculated in said prediction step and the density distribution detected in said detection step,
wherein, in said determination step, the next timing of radiation imaging is determined to, at a connection portion between the density distribution of an image obtained by latest radiation imaging and the density distribution of an image after movement, make a sum of the density distributions equal a predetermined radiopaque dye density when the density distribution detected in said detection step moves at the moving speed calculated in said prediction step.

* * * * *